(12) United States Patent
Edwards

(10) Patent No.: US 6,425,853 B1
(45) Date of Patent: Jul. 30, 2002

(54) TREATING BODY TISSUE BY APPLYING ENERGY AND SUBSTANCES WITH A RETRACTABLE CATHETER AND CONTAINED COOLING ELEMENT

(75) Inventor: Stuart D. Edwards, 658 Westridge Dr., Portola Valley, CA (US) 94028

(73) Assignee: Stuart D. Edwards, Portola Valley, CA (US)

(*) Notice: Subject to any disclaimer, the term of this patent is extended or adjusted under 35 U.S.C. 154(b) by 0 days.

(21) Appl. No.: 09/339,473

(22) Filed: Jun. 23, 1999

(51) Int. Cl.$^7$ .................................................. A61F 2/00
(52) U.S. Cl. ...................................................... 600/29
(58) Field of Search .................. 600/29–32; 604/19–22, 604/48, 500–502, 514–517, 506; 607/96, 98–102, 113, 138

(56) References Cited

U.S. PATENT DOCUMENTS 5,921,954 A * 7/1999 Mohr, Jr. et al. ............. 604/53
6,077,257 A * 6/2000 Edwards et al. ............ 604/504

* cited by examiner

Primary Examiner—John P. Lacyk

(74) Attorney, Agent, or Firm—Michael A. Glenn; Christopher Peil

(57) ABSTRACT

The invention provides a method and system for treatment for body structures, especially internal body structures involving unwanted features or other disorders, that does not require relatively invasive surgery, and is not subject to other drawbacks noted with regard to the known art. A relatively minimally invasive catheter including a contained cooling element is inserted into the body. The distal and proximal end of the catheter are extended or retracted or some combination thereof so as to achieve optimal delivery of treatment. Treatment of the body structures is applied using the electrodes embedded in the cooling element, and the unwanted features or disorders are relatively cured using the applied treatments. In a preferred embodiment, the applied treatments can include application of energy or substances, including application (such as of radio frequency energy, microwave energy, or laser or other electromagnetic energy) or substances (such as collagen or other bulking, plumping, or shaping agents; saline or other energy-receiving electrolytes; astringents or other debulking, reducing, or shaping agents; antibiotics or other bioactive, chemoactive, or radioactive compounds). In a preferred embodiment, more than one applied treatment can be performed, either in conjunction, in parallel, or seriatim, so as to achieve a combined effect more substantial than any one individual such applied treatment.

12 Claims, 2 Drawing Sheets

TREATING BODY TISSUE BY APPLYING ENERGY AND SUBSTANCES WITH A RETRACTABLE CATHETER AND CONTAINED COOLING ELEMENT

RELATED APPLICATIONS

Inventions described herein can be used in combination or conjunction with inventions described in the following patent application(s):

application Ser. No. 08/731,372, filed Oct. 11, 1996, claiming priority dates at least as early as Jun. 24, 1994, in the name of Stuart D. Edwards, and all pending cases claiming priority thereof;

application Ser. No. 09/026,316, filed Feb. 19, 1998, in the name of Stuart D. Edwards, and all pending cases claiming priority thereof;

application Ser. No. 08/677,811, filed Jul. 10, 1996, in the name of Lawrence J. Mohr, Jr., and Stuart D. Edwards, titled "Treating Aneurisms by Applying Hardening/Softening Agents to Hardenable/Softenable Substances," and all pending cases claiming priority thereof;

application Ser. No. 08/717,612, filed Sep. 20, 1996, in the name of Stuart D. Edwards and Steven Marcus, titled "Ablation of Rectal and Other Internal Body Structures," assigned to the same assignee, and all pending cases claiming priority thereof; and application Ser. No. 08/795,656, filed Feb. 6, 1997, in the name of Stuart D. Edwards and Muta M. Issa, titled "Treating Urinary and Other Body Structures," assigned to the same assignee, and all pending cases claiming priority thereof.

These applications are each hereby incorporated by reference as if fully set forth herein. These applications are collectively referred to herein as "Incorporated Disclosures."

BACKGROUND OF THE INVENTION

1. Field of the Invention

This invention relates to treating body tissue, particularly to treating body tissue by altering the shape or volume of that body tissue using energy or substances deployed from an interstitial location in the body.

2. Related Art

Human beings and other animals are subject to a number of medical disorders, including those in which a body structure is subject to unwanted features or is otherwise dysfunctional. For example, the body structure can include muscular tissue, mucosal tissue, gastro-intestinal tissue, lumen walls, stenotic locations in lumens or interstitial locations, or tumors or other cancerous or precancerous conditions. The unwanted features can for example include being distended or engorged, being unduly large or small, being misshapen, having cysts or tumors, or having undesirable growths. Other dysfunctions can include aneurysms, diverticuli, fissures, hemorrhoids, tumors, or simply an inability for the body structure to perform its proper function.

Medical disorders of these kinds can be particularly critical when they involve important areas of the body, including the cardiovascular system, the gastro-intestinal tract, the genito-urinary system, the pulmonary system, the locomotor system, the vascular system, or other body systems. For a first example, disorders involving body structures in the gastro-intestinal tract can lead (at a first end thereof) to inadequate operation of the esophageal sphincter, to gastro-intestinal reflux, or to Barrett's esophagus. For a second example, disorders involving body structures in the gastro-intestinal tract can lead (at a second end thereof) to fecal or urinary incontinence.

Surgical treatment of such disorders can be relatively invasive and labor-intensive. This has the drawbacks of incurring relatively high expense, of incurring relatively high risk (in some cases) of damage to important nerves, and of producing iatrogenic effects that are relatively hazardous to the patient.

The use of radio frequency (RF) to ablate tissue in the body (such as heart muscle tissue) is known in the art of cardiac treatment. However, known systems using RF energy are still subject to several drawbacks. One known problem is that it can be difficult to block the flow of bodily fluids and gases into an area of the body where tissue ablation is taking place. Bodily fluids can dissipate and detrimentally absorb the energy to be applied to the tissue to be ablated. Dissipation of bodily fluids detracts from the goal of treatment of diseased tissue.

A second problem in the known art involves directing and positioning the electrodes in the body cavity or orifice. Difficulties in accurately positioning the electrodes in the target orifice detract from treatment. Frequently, unhealthy tissue remains untreated while healthy tissue is compromised. Difficulties in directing and positioning the electrodes are particularly problematic because one of the goals of treatment is to minimize collateral damage to healthy tissue and to completely treat diseased tissue.

A third problem in the known art involves providing a cooling element that does not detract from the goal of successful treatment. Some known systems rely upon infusion of a cooling liquid into the targeted area for treatment. While such infusion of liquid can minimize thermal injury to the patient, it is not always applicable in all parts of the body. For example, infusion of cooling liquids into an internal body cavity such as a bladder, uterus, or stomach can rupture the targeted organ or cause osmotic imbalance within the tissue.

A fourth problem in the known art involves difficulty in the simultaneous use of complimentary technology. Known systems do not provide for optimal, simultaneous use of auxiliary tools for visualization, feedback technology and drug administration.

A fifth problem in the known art involves protection and stimulation of nerve bodies in the tissue. Known systems do not provide for protection of sensitive nerves during treatment or allow nerves to be identified and stimulated. This is particularly problematic because many tissue disorders arise because afferent and efferent nerves are either under-stimulated or over-stimulated.

Accordingly, it would be advantageous to provide a method and apparatus for treatment for body structures, especially internal body structures involving unwanted features or other disorders, that does not require relatively invasive surgery, and is not subject to other drawbacks noted of the known art. This advantage is achieved in an embodiment of the invention in which a relatively minimally invasive catheter is inserted into the body, treatment of the body structures is applied using electrodes that extend through a cooling element, so the unwanted features or disorders are ameliorated using the applied treatments. Unlike known devices, positioning of the electrodes and cooling element can be achieved without disturbing the entire length of the catheter because the electrodes and cooling element are mounted on a section of the catheter that is disposed to extend or retract. The applied treatments can include application of energy or substances, including application of energy (such as of radio frequency energy, microwave energy, laser or other electromagnetic energy, or ultrasound or other wave energy) or substances (such as collagen or other bulking, plumping, or shaping agents; saline or other energy-receiving electrolytes; astringents or other debulking, reducing, or shaping agents; or antibiotics or other bioactive, chemoactive, or radioactive compounds). Rupture, osmotic damage and other dangers associated with infusion of cooling liquids are avoided because the electrodes that apply such energy are embedded in a contained cooling element. The catheter also includes probes disposed to identify specific nerves for subsequent stimulation or protection. More than one applied treatment can be performed, either in conjunction, in parallel, or seriatim, so as to achieve a combined effect more substantial than any one applied treatment by itself.

SUMMARY OF THE INVENTION

The invention provides a method and system for treatment for body structures, especially internal body structures involving unwanted features or other disorders, that does not require relatively invasive surgery, and is not subject to other drawbacks of the known art. A relatively minimally invasive catheter including a contained cooling element is inserted into the body. The distal and proximal end of the catheter are extended or retracted or some combinations thereof so as to achieve optimal delivery of treatment. Treatment of the body structures is applied using the electrodes and the cooling element, so the unwanted features or disorders are ameliorated using the applied treatments.

In a preferred embodiment, the applied treatments can include application of energy or substances, including application of energy (such as of radio frequency energy, microwave energy, laser or other electromagnetic energy, or ultrasound or other wave energy) or substances (such as collagen or other bulking, plumping, or shaping agents; saline or other energy-receiving electrolytes; astringents or other debulking, reducing, or shaping agents; or antibiotics or other bioactive, chemoactive, or radioactive compounds).

In a preferred embodiment, more than one applied treatment can be performed, either in conjunction, in parallel, or seriatim, so as to achieve a combined effect more substantial than any one individual such applied treatment.

In preferred embodiments, the unwanted features or other disorders include one or more of the following:

Barrett's disease, other growths on the esophageal lining or near the esophageal sphincter, or otherwise relatively near an ingestive end of the gastro-intestinal system;

fecal incontinence or other failures of the musculature or sphincters relatively near an excretory end of the gastro-intestinal system;

menorrhagia, fibroids, cysts or other failures of the musculature of the female reproductive system;

obesity or other failures of the musculature and enervation at the digestive end of the gastro-intestinal system;

urinary incontinence or other failures of the musculature or sphincters relatively near an excretory end of the gastro-intestinal system.

DETAILED DESCRIPTION OF THE PREFERRED EMBODIMENTS

In the following description, a preferred embodiment of the invention is described with regard to preferred process steps and data structures. Those skilled in the art would recognize after perusal of this application that embodiments of the invention can be implemented using circuits adapted to particular process steps described herein, and that implementation of the process steps described herein would not require undue experimentation or farther invention.

System Elements

Figure 1:
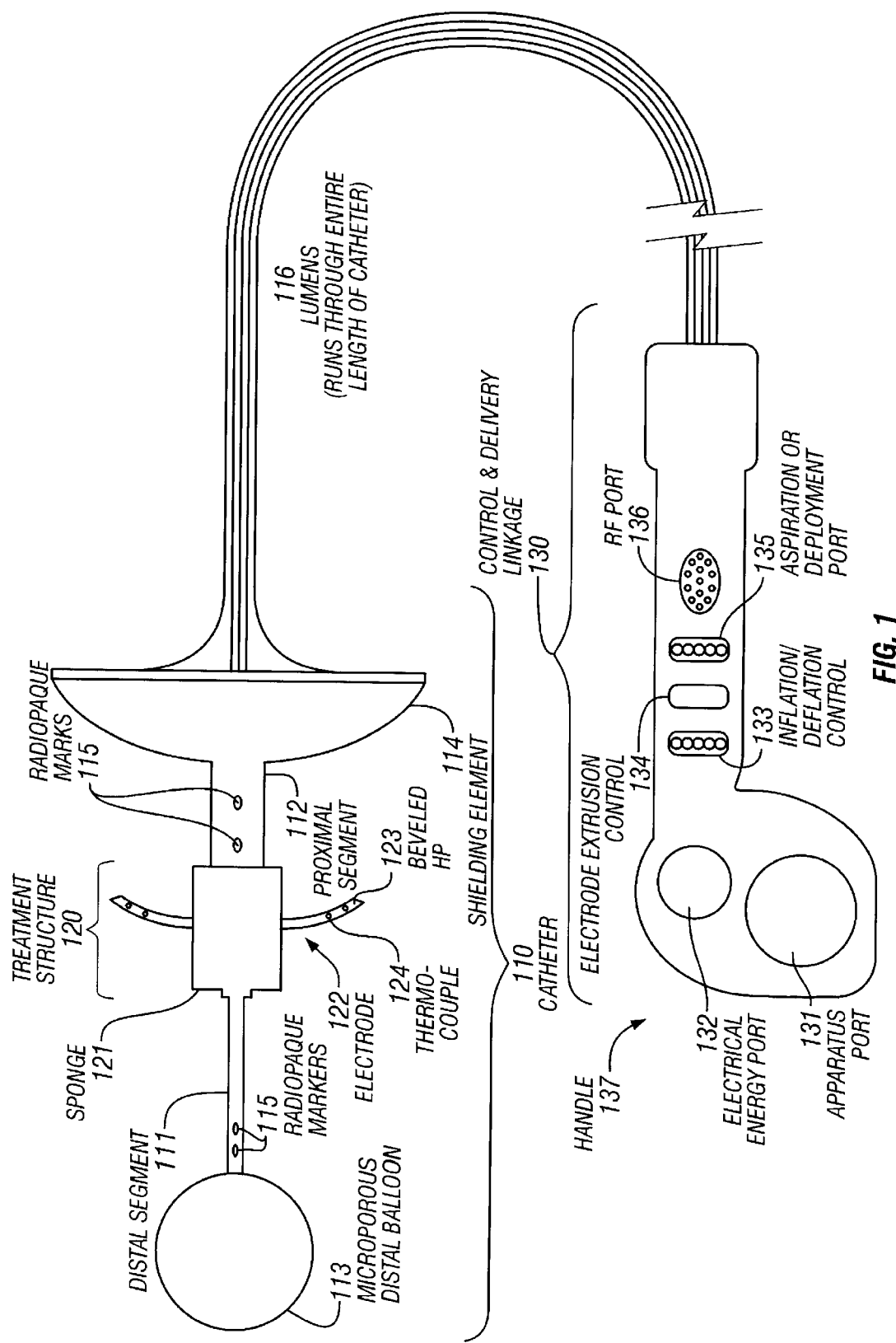
FIG. 1 is a block diagram of a system for treating tissue associated with the rectal sphincter, esophagus, urethra and other internal body structures using a catheter and electrode assembly.

FIG. 1 is a block diagram of a system for treating tissue associated with the rectal sphincter, esophagus, urethra and other internal body structures using a catheter and electrode assembly.

The catheter 110 includes a distal segment 111 and a proximal segment 112. The distal segment 111 includes a microporous distal balloon 113. The proximal segment includes a shielding element 114 and a treatment structure 120. Both the distal segment and proximal segment 112 include radiopaque markers 115 for use in flouroscopy. Taken together, the distal balloon 113, distal segment 111, the treatment structure 120, the proximal segment 112 and shielding element 114 are linearly contiguous and form a short, flexible, unit. Two or more lumens 116 run through the entire interior length of the catheter 110.

The diameter and combined length of the distal segment 111 and the proximal segment 112 are responsive to the size and accessibility of the targeted orifice. The catheter 110 may be introduced into the target tissue by itself, using an introducer sheath 117 or over a guidewire 118. Either before or after insertion, both the distal segment 111 and the proximal segment 112 can be completely or partially extended or retracted relative to each other. For example, it is possible to completely retract the distal segment 111 so that the treatment structure 120 is immediately adjacent to the distal balloon 113. Likewise, it is possible to retract the proximal segment 112 so that the treatment structure 120 is immediately adjacent to the shielding element 114. Correct positioning of the treatment structure in an orifice or internal body organ is achieved by the retraction or extension of the distal segment 111, or the retraction or extension of the proximal segment 112, or some combination thereof. An additional measure of position is obtained by looking to the incremental markings (in units of less than a centimeter) that are located on the exterior of the catheter.

In a preferred embodiment, the distal segment 111 is disposed for insertion into a cavity of the body. In a preferred embodiment, this cavity can include a female urethra and bladder. In alternative embodiments, the cavity may include one or more of, or some combination of, the following:

Any portion of the bronchial system, the cardiovascular system, the genito-urinary tract, the lymphatic system, the pulmonary system, the vascular system, the locomotor system, the reproductive system, or other systems in the body;

Any biologic conduit or tube, such as a biologic lumen that is patent or one that is subject to a stricture;

Any biologic cavity or space, such as a cyst, a gland, a sinus, a layered structure or striation, or a medical device implanted or inserted in the body;

Any biologic operational structure, such as a gland, or a muscular or other organ (such as the colon, the diaphragm, the heart, a uterus, a kidney, a lung, the rectum, an involuntary or voluntary sphincter);

Any other biologic structure, such as a herniated body structure, a set of diseased cells, a set of displastic cells, a surface of a body structure (such as the sclera), a tumor, or a layer of cells (such as fat, muscle, or skin). or Any other biologic structure, such as a surgical structure, such as an opening in the body created by a surgical incision, by insertion of a medical implant, by laporoscopy, or otherwise.

The distal balloon 113 is disposed for inflation, preferably after the catheter 110 has been inserted into the body.

The inflated distal balloon 113 can perform one or more of, or some combination of, the following functions:

- The distal balloon 113 can position the catheter 110 in a relatively fixed position within the body. For example, in a preferred embodiment in which the catheter 110 is inserted into the urethra, the inflated distal balloon 113 can prevent the catheter 110 from being pulled back out of the urethra.
- The distal balloon 113 can isolate the catheter 110 (and its treatment structure 120) from the rest of the body. For example, in a preferred embodiment in which the catheter 110 is inserted into the rectum, the inflated distal balloon 113 can prevent treatment substances and any substances that result from treatment (such as killed cells) from passing into other regions of the body. Such isolation of the catheter 110 and treatment structure also prevents the area targeted for treatment from being contaminated with fecal matter.
- The distal balloon 113 can serve as a sensor. For example, the distal balloon 113 can include an x-ray opaque element or an x-ray reflector, so as to enable medical or other personnel to determine a position of the catheter 110 using a fluoroscope or an x-ray device.
- The distal balloon 113 can serve as a drug delivery device. For example, the flowable drugs can be exuded from the micropores in the distal balloon 113 to condition the tissue or treat it. In a preferred embodiment, these drugs could include analgesics, antibiotics, anti-inflammatory or chemotherapeutic agents, narcotics and other pharmaceutical substances.

The shielding element 114 is also disposed for inflation, preferably after the catheter 110 has been inserted into the body.

Similarly, the shielding element 114 can perform one or more of, or some combination of, the following functions:

- The shielding element 114 can position the catheter 110 in a relatively fixed position within the body. For example, in a preferred embodiment in which the catheter 110 is inserted into the urethra, the shielding element 114 can prevent the catheter 110 from being inserted further into the urethral canal.
- The shielding element 114 can isolate the catheter 110 and the treatment structure 115 from the rest of the body. For example, in a preferred embodiment in which the catheter 110 is inserted into the esophagus, the shielding element 114 can prevent treatment substances and any substances that result from treatment (such as killed cells) from passing into other regions of the body.
- The shielding element 114 can serve as a sensor. For example, the shielding element 114 can include an x-ray opaque element or an x-ray reflector, so as to enable medical or other personnel to determine a position of the catheter 110 using a fluoroscope or an x-ray device.
- The shielding element 114 can serve as a delivery element for electromagnetic (or ultrasonic, or other) energy. For example, the shielding element 114 can include a set of metallic (or metallic coated) elements, or can be coupled to a basket having a set of electrodes, for delivery of RF or other electromagnetic energy.
- The shielding element 114 can serve as a drug delivery device. For example, the flowable drugs can be exuded from the micropores in the shielding element 114 to condition the tissue or treat it. In a preferred embodiment, these drugs could include analgesics, antibiotics, anti-inflammatory or chemotherapeutic agents, narcotics and other pharmaceutical substances.

The treatment structure 120 includes a sponge 121 and one or more unipolar electrodes 122.

The sponge 121 has a cylindrical, marshmallow-like shape and is comprised of polyurethane, pebax or other biologically inert material. Associated with the sponge 121 are at least two lumens 116. An integrated fluid pump 140 can be disposed to infuse the lumen 116 and the sponge 121 with chilled liquid. Chilled liquid can circulate freely through the lumen 116 into the sponge 121 and then back through a lumen 116 of the catheter 110. The cells and absorptive tissue of the sponge 121 contain the cooling liquid and prevent it from being exuded into the body. The sponge 121 can perform one or more of, or some combination of the following functions:

- The sponge 121 can cool body tissues that it is in physical contact with. For example, in a preferred embodiment in which the catheter 110 is inserted into a urethra, the sponge 121 can prevent thermal damage from being inflicted upon healthy tissue while allowing treatment to be directed in a specific, targeted area.
- The sponge 121 prevents cooling liquid from rupturing a targeted organ or causing osmotic damage to the cells of that organ. For example, in a preferred embodiment in which the catheter 110 is inserted into a urethra, the sponge 121 contains all the cooling liquid and prevents the liquid from contaminating the interior of the organ.
- The sponge 121 can absorb dead cells and transport them from the treatment area when the catheter 110 is removed. For example, the dead cells from debrided tissue can be absorbed into the structure of the sponge 121 and removed from the body when the catheter 110 is withdrawn.
- The unipolar electrodes 122 are spaced radially around the surface of the sponge so that the beveled tip 123 of each electrode can push through the sponge to enter the tissue. The electrodes 122 can be straight or curvilinear. Whether straight or curvilinear, the electrodes 122 can be disposed after deployment at any angle to the catheter, such as at an angle less than 90 degrees or at an angle more than 90 degrees. Each electrode is associated with a lumen 116. Each electrode 122 can be individually manipulated to treat tissue by ablation, cell death, desication, or other aspect of delivery of RF energy to tissue. A thermocouple 124 is mounted on the shaft of each electrode 116. These thermocouples 124 are used to monitor tissue surface temperature.

In alternative embodiments, the unipolar electrodes 122 can be disposed to treat tissue using other techniques, such as by emission of other forms of energy or by emission of substances. These can include one or more of, or some combination of, any of the following:

bipolar RF electrodes;

chemical treatment, such as acid, antibiotics, enzymes, or other bioactive, chemoactive, or radioactive substances;

heat, such as using heated saline or other heated substances;

infrared energy, such as from an infrared laser or a diode laser;

microwave energy, such as electromagnetic energy in the about 915 megahertz to about 2.45 gigahertz range;

optical energy, such as from a laser;

other electromagnetic energy, including direct current or ELF (extremely low frequency);

sonic energy, including ultrasound.

In a preferred embodiment, the electrodes 122 can also be disposed to pre-condition or pre-treat tissue so as to be conditioned, sensitized, or otherwise prepared for treatment. In a preferred embodiment, the pre-treatment includes exuding saline for absorption into the treated tissue. The absorbed saline acts to enhance reception of electromagnetic (particularly RF) energy by the tissue.

In alternative embodiments, the electrodes 122 can be disposed to pre-condition or pre-treat tissue using other techniques, such as by emission of other forms of energy or by emission of other substances. These can include any of the diagnostic probes, forms of energy or substances used for treatment, and can also include one or more of, or some combination of, any of the following:

an element capable of identifying, modifying and modulating nerve cells;

a bulking, plumping, or supportive agent, such as a collagen, a gel, or a stent;

a debulking, deplumping, or astringent or restrictive agent, such as an acid, an enzyme, or a physical constraint such as an elastic or wire; or a shaping or reshaping agent, such as a cutting element or a stent.

In a preferred embodiment, the electrodes 122 can also be disposed to post-condition or post-treat tissue so as to be healed or otherwise repaired after treatment. In a preferred embodiment, the post-treatment includes exuding pharmaceutical agents such as analgesics, antibiotics or anti-inflammatory drugs, for absorption into the treated tissue and adjacent tissues. The post-treatment enhances the ability of the treated tissue and adjacent tissues to recover from treatment.

In alternative embodiments, the electrodes 122 can be disposed to post-condition or post-treat tissue using other techniques, such as by emission of other forms of energy or by emission of other substances.

The catheter and electrode assembly 110 is operated by manipulating the control and delivery linkage 130. The control and delivery linkage 130 includes a apparatus port 131, an electrical energy port 132, an inflation/deflation coupling 133, an electrode extrusion control 134, a set of aspiration or deployment ports 135, an RF port 136 and a handle 137.

The apparatus port 131 can be coupled to visualization apparatus, such as fiber-optic devices or flouroscopy equipment, to allow internal viewing of the orifice. In a preferred embodiment, the apparatus port 131 can also be coupled to other appliances including devices for insertion and probing into the body, such as a colonoscope, anoscope, a laparoscope, an endoscope, or another type of catheter. These devices are preferably controlled from a location outside the body, such as an instrument in an operating room or an external device for manipulating the inserted catheter 110.

In an alternative embodiment, the apparatus port 131 may be coupled to devices that are implanted or inserted into the body, and manipulated from inside or outside the body during a medical procedure. For example the apparatus port 131 may be coupled to a programmed AICD (artificial implanted cardiac defibrillator), a programmed glandular substitute (such as an artificial pancreas), or other device for use during surgery or in conjunction with other medical procedures.

The electrical energy port 132 includes a conductive element that can be coupled to a source of electrical energy, such as a battery, a generator or a wall socket.

The inflation/deflation coupling 133 includes a receptor for coupling to a source of air, liquid or other flowable substance. The flowable substances can be used to inflate the distal balloon 113 and the shielding element 114 in response to input or positive pressure to the inflation/deflation coupling 133.

The electrode extrusion control 134 includes an element that is disposed to select and extend one or more electrodes 121.

The substance aspiration or deployment ports 135 include receptors for aspirating inflatable substances from or near the targeted tissue, and for deploying flowable substances into or near the distal balloon 113, the shielding element 114, the electrodes 122 and/or the sponge 121. Aspiration can be achieved by coupling the aspiration or delivery elements 116 to an integrated fluid pump 140 or other suction element, so as to generate suction to drain flowable material from the body. Delivery can be achieved by coupling the aspiration or delivery elements 116 to an integrated pump 140 or other pressure element, and to a source of flowable substances, so as to generate pressure to source flowable material into the body.

The RF port 136 includes a receptor for coupling to a source of RF energy or other source of therapeutic energy such as a laser, light emitting diode, or a generator of x-rays, gamma rays or beta rays.

The handle 137 is disposed for manipulation by medical or veterinary personnel and can be shaped for being held in the hand. The visualization port 131, the electrical energy port 132, the inflation/deflation coupling 133, the electrode extrusion control 134 and the set of aspiration and deployment ports 135 are all mounted in the handle 137 to allow for easy operation.

Treatment Device Used for Urinary Incontinence

Figure 2B:
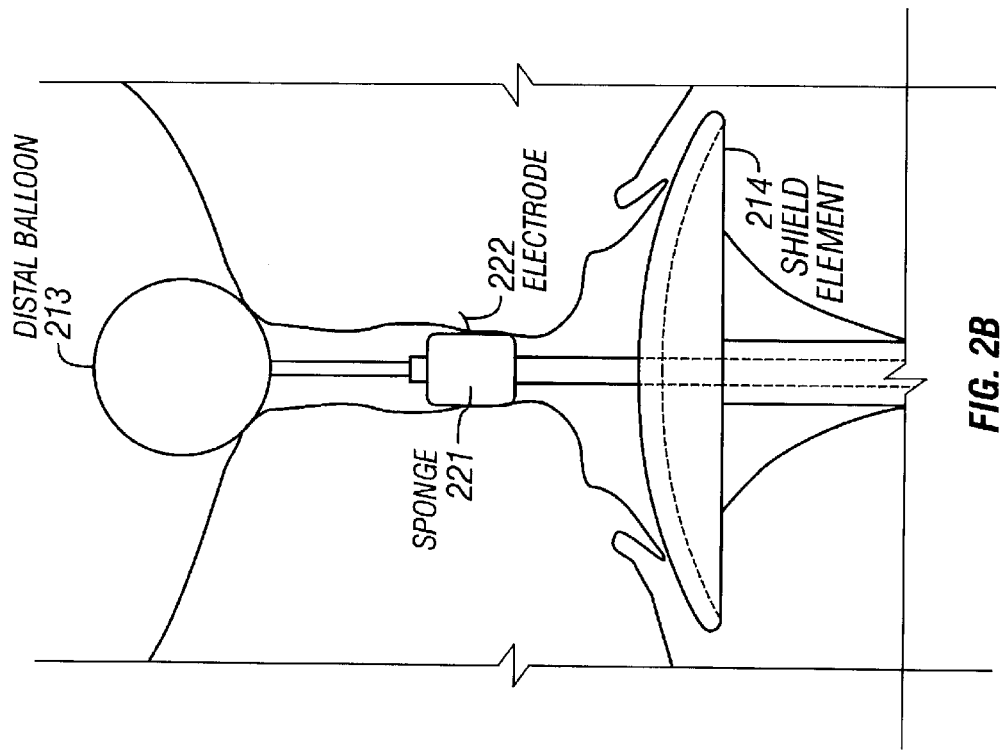
FIG. 2 shows a drawing of a system for a treatment of a body structure, for possible application to structures implicated in urinary incontinence.
Figure 2A:
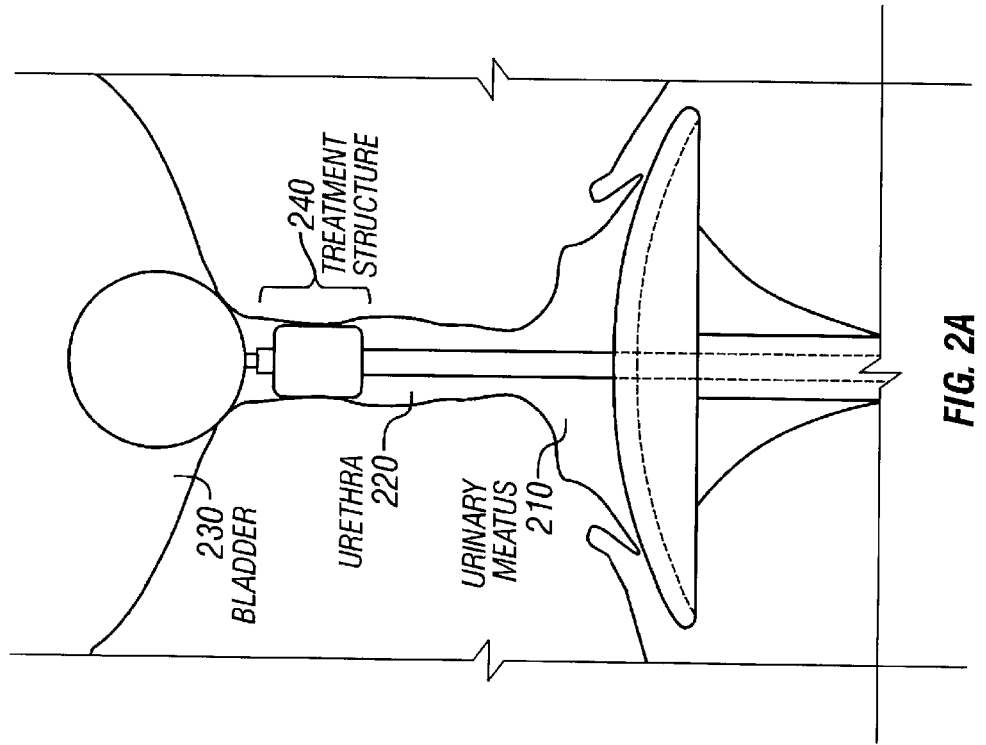

FIG. 2 shows a drawing of a system for a treatment of a body structure, for possible application to structures implicated in urinary incontinence in women.

The device 200 is introduced into a female urinary meatus 210 in an upward and backward motion, in much the same way that a Foley catheter is introduced into a urethra 220. In operation, a distal balloon is positioned at one of the bladder 230 and the shielding element is positioned at the opposite end. Taken together, the distal balloon and shielding element prevent the device 200 from being mistakenly drawn out of the urethra 220.

In operation, the device 200 has a substantially greater length-to-width ratio, so as to fit into the bladder and urethra transurethally.

In an alternative embodiment, the device 200 is inserted into a glans penis.

The tissue(s) targeted for treatment is identified using fluoroscopy, ultrasound or endoscopy.

In operation, the proximal and distal members of the catheter are extended to achieve optimal position of the electrodes. In an alternative embodiment, probes coupled to the microporous distal balloon 213 or treatment structure interact with the nervous system to direct placement of the electrodes 222.

After the electrodes 222 have been positioned, the distal balloon 213 is inflated to achieve isolation of the targeted tissue. The sponge 221 is infused with a circulating liquid. The electrodes 222 are extruded into the surface of the urethra 220, and possibly into tissue there-behind. The proximal shielding element 214, distal balloon 213, sponge 221 and electrode 222 apply pre-conditioning, treatment, and post-treatment to those tissues.

The treatment element 240 operates to create a pattern of lesions. Creation of these lesions has the effect of causing the involuntary sphincter to shrink so that urine does not seep through. The treatment elements can also operated to reshape the bladder with respect to the bladderneck and detruser muscles in such a way as to maximize retention of urine. In an alternative embodiment, muscle contraction (and the consequent shrinkage of the involuntary sphincter) can be achieved by application of chemical stimulation. After operation, the urinary sphincter and the urethra 220 are capable of a more tightly sealed closure, so as to militate against urinary incontinence. In other alternative embodiments, the treatment elements are disposed to perform ablation or debulking, bulking or plumping, or otherwise to perform shaping or reshaping, of those tissues.

Following pre-treatment, treatment and post-treatment, the integrated fluid pump is turned off. The distal balloon 213 is deflated is allow easy removal from the body.

Generality of the Invention

The invention has substantial generality of application to various fields for biopsy, diagnostic procedures, or treatment of medical conditions.

As noted above, the invention can be used in any area of the body, including the biologic systems and locations noted herein. The invention can be used for the general purpose of reducing, plumping, or reshaping body structures, tissues, or regions of the body otherwise empty (or filled with biologic substances).

For examples, the invention can be used in one or more of, or some combination of, the following:

In the head and neck, such as the cheeks, eyes, sinuses, middle ear, nostrils, inner ear, Eustachian tubes, pharynx, larynx, or other structures;

For the purpose of reforming damaged body parts, for the purpose of reshaping misshapen body parts, dilating occluded tissues, or for cosmetic effects; or For the purpose of replacing the volume filled by body parts that are missing, whether due to congenital defect, infection, or surgery.

Alternative Embodiments

Although preferred embodiments are disclosed herein, many variations are possible which remain within the concept, scope, and spirit of the invention, and these variations would become clear to those skilled in the art after perusal of this application.

What is claimed is:

1. A method for applying treatment incidental to a first treatment, including steps for:

positioning a medical device substantially within a body of a patient, said medical device including (a) a catheter having a first element for emitting a flowable substance, and (b) a second element for affecting said flowable substance so as to affect tissue near said flowable substance; and pre-conditioning selected tissue for said first treatment using said first element and second element.

2. A method as in claim 1, including steps for post-treating said selected tissue in response to said first treatment using said first element and second element.

3. A method as in claim 1, wherein said selected tissue is subject to Barrett's Disease.

4. A method as in claim 1, wherein said second element includes a plurality of substantially differing frequencies of electromagnetic energy.

5. A method as in claim 4, wherein said differing frequencies include at least two of: radio frequency energy, microwave energy, and visible light.

6. A method as in claim 1, wherein said selected tissue is substantially near a sphincter.

7. A method as in claim 6, wherein said sphincter is a rectal sphincter.

8. A method as in claim 6, wherein said sphincter is a urinary sphincter.

9. A method as in claim 6, wherein said sphincter is an esophageal sphincter.

10. A method as in claim 1, wherein said selected tissue is treated to affect a condition of incontinence.

11. A method as in claim 10, wherein said condition of incontinence includes fecal incontinence.

12. A method as in claim 10, wherein said condition of incontinence includes urinary incontinence.

* * * * *